United States Patent
Ellies et al.

(10) Patent No.: US 8,460,642 B2
(45) Date of Patent: Jun. 11, 2013

(54) BOLDLINE COMPOUNDS FOR PROMOTING BONE GROWTH

(75) Inventors: Debra Ellies, Parkville, MO (US); William Rosenberg, Overland Park, MO (US)

(73) Assignee: OssiFi, Inc., Kansas City, KS (US)

( * ) Notice: Subject to any disclaimer, the term of this patent is extended or adjusted under 35 U.S.C. 154(b) by 0 days.

(21) Appl. No.: 13/456,060

(22) Filed: Apr. 25, 2012

(65) Prior Publication Data

US 2012/0301509 A1 Nov. 29, 2012

Related U.S. Application Data

(63) Continuation of application No. 12/571,623, filed on Oct. 1, 2009, now Pat. No. 8,188,065.

(60) Provisional application No. 61/102,084, filed on Oct. 2, 2008.

(51) Int. Cl.
| | |
|---|---|
| *A61K 8/18* | (2006.01) |
| *A61K 39/395* | (2006.01) |
| *A61K 33/42* | (2006.01) |
| *A61K 33/22* | (2006.01) |
| *A61K 33/08* | (2006.01) |
| *A61K 33/06* | (2006.01) |
| *A61K 31/59* | (2006.01) |
| *A61K 31/44* | (2006.01) |
| *A61K 31/135* | (2006.01) |

(52) U.S. Cl.
USPC .......... 424/49; 424/141.1; 424/484; 424/602; 424/657; 424/689; 424/698; 514/167; 514/284; 514/654

(58) Field of Classification Search
USPC ................ 424/49, 141.1, 484, 602, 657, 689, 424/698; 514/167, 284, 654
See application file for complete search history.

(56) References Cited

U.S. PATENT DOCUMENTS

| | | |
|---|---|---|
| 2003/0143258 A1 | 7/2003 | Knaack et al. |
| 2004/0024471 A1 | 2/2004 | Ferree |
| 2005/0031667 A1 | 2/2005 | Patel et al. |

FOREIGN PATENT DOCUMENTS

| | | |
|---|---|---|
| WO | WO 90/12574 | 11/1990 |
| WO | WO 2004/084801 | 10/2004 |

OTHER PUBLICATIONS

International Search Report and Written Opinion dated May 7, 2010, issued in related International Patent Application No. PCT/US2009/059172, filed Oct. 1, 2009.
Cecil Textbook of Medicine, 21$^{st}$ Edition, vol. 1, pp. 1060-1074; Goldman et al., (eds), published by W. B. Saunders Company, (PA), 2000.

*Primary Examiner* — Raymond Henley, III
(74) *Attorney, Agent, or Firm* — Kilpatrick Townsend & Stockton LLP

(57) ABSTRACT

The present invention provides a method of promoting bone growth in a subject in need thereof, by administering to the subject a therapeutically effective amount of a compound of Formula I. The present invention also provides methods for the treatment of renal disease and cancer.

13 Claims, 1 Drawing Sheet

BOLDLINE COMPOUNDS FOR PROMOTING BONE GROWTH

CROSS-REFERENCES TO RELATED APPLICATIONS

This application is a Continuation of U.S. Application No. 12/571,623, filed Oct. 1, 2009 now U.S. Pat. No. 8,188,065, and claims priority to U.S. Provisional Application No. 61/102,084, filed Oct. 2, 2008, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. 5R44AR052962, awarded by the NIH. The Government has certain rights in this invention.

BACKGROUND OF THE INVENTION

It is well-understood that bone formation is indicated for treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc.

Increasing bone mineralization to treat conditions characterized at least in part by increased bone resorption, such as osteopenia, bone fractures, osteoporosis, arthritis, tumor metastases, Paget's disease and other metabolic bone disorders, using cathepsin K inhibitors and TGF-beta binding proteins, etc., are well-known as shown by U.S. Publication No. 2004/0235728 to Selwyn Aubrey Stoch, published Nov. 25, 2004, and Mary E. Brunkow et al., U.S. Pat. No. 6,489,445 and U.S. Publication No. 2004/0009535, published Jan. 15, 2004. In the Brunkow '535 publication and '445 patent, the TGF-beta binding proteins include Sost polypeptide (full length and short peptide) antibodies that interfere with the interaction between the TGF-beta binding protein sclerostin and a TGF-beta superfamily member, particularly a bone morphogenic protein. All of the diseases named above are due to a systemic loss of bone mineral and thus the administration of the antibody therapeutic is for systemic (whole body) increase in bone mineral density.

In the Brunkow '535 publication and '445 patent, the binding proteins preferably bind specifically to at least one human bone morphogenic protein (BMP) among BMP-5 and BMP-6.

U.S. Pat. No. 6,395,511 to Brunkow, et al. teaches a novel family of human TGF-beta binding proteins and nucleic acids encoding them. The protein binds to at least human bone morphogenic protein-5 and human bone morphogenic protein-6.

Sclerosteosis is a progressive sclerosing bone dysplasia. Sclerostin (the Sost gene) was originally identified as the sclerosteosis-causing gene. Sclerostin was intensely expressed in developing bones of mouse embryos. Punctuated expression of sclerostin was localized on the surfaces of both intramembranously forming skull bones and endochondrally forming long bones. The physiological role of sclerostin remains to be elucidated. However, it is known that loss of function mutations in Sost cause a rare bone dysplasia characterized by skeletal overgrowth.

In U.S. Publication No. 2006/0165799, published Jul. 27, 2006, teaches a bone-filling composition for stimulating bone-forming and bone-consolidation comprising biocompatible calcium sulfate and viscous biopolymers. The composition is intended to be administered easily into the missing part of injured bone without diffusing to surrounding organs.

In U.S. Pat. No. 5,939,039, issued in 1999 teaches the processes to yield unique calcium phosphate precursor minerals that can be used to form a self-setting cement or paste. Once placed in the body, these calcium phosphate cements (CPC) will be resorbed and remodeled (converted) to bone.

For example, calcium phosphate particles prepared in accordance with the '039 patent can be used in any of the orthopedic or dental procedures known for the use of calcium phosphate; the procedures of bone filling defect repair, oncological defect filling, craniomaxillofacial void filling and reconstruction, dental extraction site filling.

U.S. Publication No. 2006/0198863 to Carl Alexander DePaula, published Sep. 7, 2006, relates to a formable ceramic composition for filling bone defects. The composition comprises ceramic beta tricalcium phosphate particles having a particle size from about 40 microns to 500 microns admixed with a hydrogel carrier containing citric acid buffer. The composition has a pH between 7.0 to 7.8 and the hydrogel component of the carrier ranges from about 1.0 to 5.0% of the composition.

Wise and SOST are understood to be closely related family members (Ellies et al., JBMR 2006 Nov.; 21(11):1738-49.). Those of ordinary skill are aware that the Wise null mutant mouse exhibits a bone phenotype (Keynote presentation at the 2005 American Society of Bone Mineral Research meeting in Nashville, Tenn. State of the Art lectures, an embryonic source of skeletal tissue. Patterning Craniofacial Development; by Robb Krumlauf, Ph.D., Stowers Institute for Medical Research, Kansas City, Mo., USA).

U.S. Publication No. 2005/025604 to Vignery published Nov. 17, 2005 shows induction of bone formation by mechanically inducing an increase in osteoblast activity and elevating systemic blood concentration of a bone anabolic agent, including optionally elevating systemic blood concentration of an antiresorptive agent.

Finally, Yanagita, *Modulator of bone morphogenic protein activity in the progression of kidney diseases, Kidney Int.*, Vol. 70, No. 6 (2006) 989-93 shows Usag-1 (also known as "Wise") protects the kidney from cisplatin insult due to BMP inhibition. See also Yanagita, *Uterine sensitization-associated gene-1 (USAG-1), a novel antagonist expressed in the kidney, accelerates tubular injury*, J. Clin. Invest., Vol. 116, No. 1 (2005) 70-9, Yanagita, *BMP antagonists: their roles in development and involvement in pathophysiology, Cytokine Growth Factor Rev.*, Vol 16, No. 3 (2005) 309-17, and Yanagita, *USAG-1: a bone morphogenic protein antagonist abundantly expressed in the kidney, Biochem. Biophys. Res. Commun.*, Vol. 316, No. 2 (2004) 490-500.

What is needed in the art is a new method for treating the bone disorders described above, as well as others. Surprisingly, the present invention meets these and other needs.

BRIEF SUMMARY OF THE INVENTION

In a first embodiment, the present invention provides a method of promoting bone growth in a subject in need thereof, comprising administering to the subject a therapeutically effective amount of a compound of Formula I:

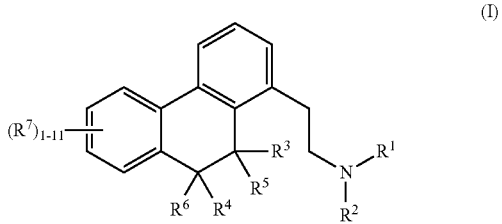

(I)

wherein each $R^1$, $R^2$, $R^4$, $R^5$, $R^6$, and $R^7$ is independently H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, $-OR^8$, $-C_{0-6}$ alkyl-$NR^8R^9$, $-SR^8$, $-C(O)R^8$, $-C_{0-6}$ alkyl-$C(O)OR^8$, $-C(O)NR^8R^9$, $-N(R^8)C(O)R^9$, $-N(R^8)C(O)OR^9$, $-N(R^8)C(O)NR^8R^9$, $-OP(O)(OR^8)_2$, $-S(O)_2OR^8$, $-S(O)_2NR^8R^9$, $-CN$, $C_{0-6}$ alkyl-cycloalkyl, heterocycloalkyl, $C_{0-6}$ alkyl-aryl or heteroaryl, wherein $R^2$ or $R^4$ combines with $R^3$ to form a bond. Alternatively, $R^4$ and $R^6$ combine to form $=O$. In addition, $R^8$ and $R^9$ are each independently H or $C_{1-6}$ alkyl. The compounds include the salts, hydrates, prodrugs and isomers thereof. Thereby promoting bone growth in the subject.

In a second embodiment, the present invention provides a method of treating renal damage, comprising administering to a subject in need thereof, a therapeutically effective amount of a compound of the present invention.

In a third embodiment, the present invention provides an orthopedic or periodontal medical device comprising a structural support, wherein an implantable portion of the structural support is adapted to be permanently implanted within a subject, wherein the implantable portion is attached to a bone, the structural support bearing at least a partial external coating comprising a compound of the present invention.

In a fourth embodiment, the present invention provides a method of treating cancer, comprising administering to a subject in need thereof, a therapeutically effective amount of a compound of Formula I.

DETAILED DESCRIPTION OF THE INVENTION

I. General

Figure 1:
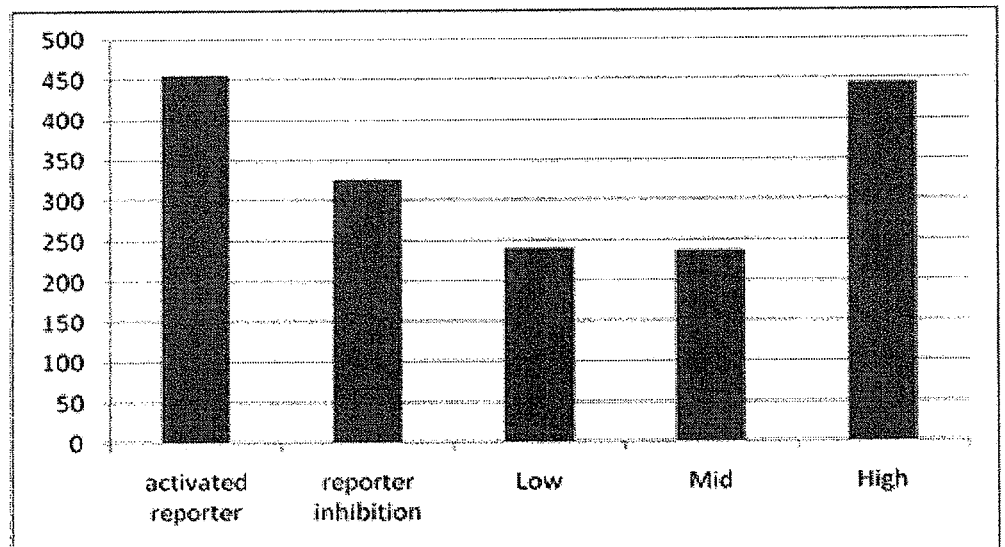
FIG. 1 shows (S)-boldine modulating the Wnt pathway to promote bone growth at doses of 2.5 ng ("low"), 60 ng ("medium"), and 125 ng ("high").

The present invention encompasses compounds, compositions and methods for promoting bone growth in a subject. The compounds of the present invention are SOST (Sclerostin) and Wise antagonists that modulate the Wnt pathway. By modulating the Wnt pathway, the compounds and compositions of the present invention promote bone growth. The bone growth can be systemic or local bone growth. The compounds and compositions of the present invention can be administered locally or systemically. The present invention also provides implantable devices for delivering the compounds and compositions of the present invention. The compounds and compositions of the present invention also act to treat renal damage and cancer.

II. Definitions

As used herein, the term "pharmaceutically acceptable excipient" refers to a substance that aids the administration of an active agent to and absorption by a subject. Pharmaceutically acceptable excipients useful in the present invention include, but are not limited to, binders, fillers, disintegrants, lubricants, coatings, sweeteners, flavors and colors.

One of skill in the art will recognize that other pharmaceutical excipients are useful in the present invention.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula $-(CH_2)_n-$, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in $-CH((CH_2)_nCH_3)-$, wherein n=0-5.

As used herein, the term "alkoxy" refers to alkyl with the inclusion of an oxygen atom, for example, methoxy, ethoxy, etc. "Halo-substituted-alkoxy" is as defined for alkoxy where some or all of the hydrogen atoms are substituted with halogen atoms. For example, halo-substituted-alkoxy includes trifluoromethoxy, etc.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, $-S(O)-$ and $-S(O)_2-$. For example, heteroalkyl can include ethers, thioethers and alkyl-amines.

As used herein, the term "cycloalkyl" refers to a saturated or partially unsaturated, monocyclic, fused bicyclic or bridged polycyclic ring assembly containing from 3 to 12 ring atoms, or the number of atoms indicated For example, $C_{3-8}$cycloalkyl includes cyclopropyl, cyclobutyl, cyclopentyl, cyclohexyl, and up to cyclooctyl.

As used herein, the term "heterocycle" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro ($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "hydrate" refers to a compound that is complexed to at least one water molecule. The compounds of the present invention can be complexed with from 1 to 10 water molecules.

Certain compounds of the present invention possess asymmetric carbon atoms (optical centers) or double bonds; the racemates, diastereomers, geometric isomers and individual isomers are all intended to be encompassed within the scope of the present invention.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "calcium salt" refers to salts containing calcium. Examples of calcium salts include, but are not limited to, calcium acetate, calcium aluminates, calcium aluminosilicate, calcium arsenate, calcium borate, calcium bromide, calcium carbide, calcium carbonate, calcium chlorate, calcium chloride, calcium citrate, calcium citrate malate, calcium cyanamide, calcium dihydrogen phosphate, calcium fluoride, calcium formate, calcium glubionate, calcium glucoheptonate, calcium gluconate, calcium glycerylphosphate, calcium hexaboride, calcium hydride, calcium hydroxide, calcium hypochlorite, calcium inosinate, calcium iodate, calcium iodide, calcium lactate, calcium lactate gluconate, calcium magnesium acetate, calcium malate, calcium nitrate, calcium nitride, calcium oxalate, calcium oxide, calcium pangamate, calcium peroxide, calcium phosphate, calcium phosphide, calcium propionate, calcium pyrophosphate, calcium silicate, calcium silicide, calcium sorbate, calcium stearate, calcium sulfate, calcium sulfide, calcium tartrate, calcium(I) chloride, dicalcium citrate, dicalcium phosphate, dodecacalcium hepta-aluminate, tricalcium aluminate, tricalcium phosphate and triple superphosphate. One of skill in the art will appreciate that other calcium salts are useful in the present invention.

As used herein, the term "site of injury or localized condition" refers to a specific location in the subject's body that is in need of treatment by the method of the present invention. For example, the injury can be a fracture and the localized condition can be a disease state (such as osteoporosis, etc.) that is limited to a particular location in the subject's body, such as a particular bone, joint, digit, hand, foot, limb, spine, head, torso, etc.

As used herein, the term "promoting bone growth" refers to the stimulation of new bone growth, or an increase in bone density or bone mineral content.

As used herein, the term "arthrodesis" refers to the artificial induction of joint ossification between two bones, often via surgery. Arthrodesis can be accomplished via bone graft, metal implants or the use of synthetic bone substitutes, among others.

As used herein, the term "bone autograft" refers to the grafting of a subject's own bone.

As used herein, the term "bone allograft" refers to the grafting of bone from one person to another person.

As used herein, the term "antiresorptive drug" refers to drugs that slow or block the resorption of bone.

As used herein, the term "bone related disease characterized by low bone mass" refers to bone having a T-score less than −1. Other methods of determining low bone mass are known by one of skill in the art.

As used herein, the term "bone fracture" refers to bone that has been cracked or broken.

As used herein, the term "spinal fusion" refers to a surgical technique for combining two or more vertebrae.

As used herein, the term "structural support" refers to a segment of the device that can be implanted in a subject (implantable portion). The structural support can be prepared from a variety of different materials, including metals, ceramics, polymers and inorganic materials, such as described below. The structural support can be coated with a variety of materials that promote bone growth.

As used herein, the term "external coating" refers to a coating of the structural support that can cover only a portion of the structural support (partial external coating) or cover the entire structural support. For example, the partial external coating can completely cover only the implantable portion of the structural support.

As used herein, the term "weakened bone" refers to bone that has a T score of less than −0.5 (less than 0.9 g/cm$^2$).

As used herein, the term "demineralized bone" refers to bone from which calcium and phosphate have been removed. The remaining material contains the osteoinductive proteins contained in the matrix. These proteins include bone morphogenetic proteins that induce new bone formation. Demineralized bone often comes in the form of "demineralized bone matrix (DBM)." DBM can be made by fresh frozen or freeze-dried bulk bone allograft, or can be made from mild acid extraction of cadaveric bone that removes the mineral phase, leaving collagen, growth factors, and noncollagenous proteins that offer the intrinsic properties of osteoconduction. DBM can also be processed in a variety of ways, ultimately resulting in a powder that is mixed with a carrier to provide the optimum handling characteristics desired by a surgeon. DBM is clinically available in gels, pastes, putty, and fabrics that have been tailored to meet the needs of the surgical procedure. Some DBM are mixed with antibiotics prior to the surgical procedure.

As used herein, the term "renal damage" refers to the inability of the kidneys to excrete waste and to help maintain the electrolyte balance of the body. Renal damage is characterized by some of the following: high blood pressure, accumulation of urea and formation of uremic frost, accumulation of potassium in the blood, decrease in erythropoietin synthesis, increase in fluid volume, hyperphosphatemia, and metabolic acidosis, among others.

As used herein, the term "osteoconductive matrix" refers to a material that can act as an osteoconductive substrate and has a scaffolding structure on which infiltrating cells can attach, proliferate, and participate in the process of producing osteoid, the organic phase of bone, culminating in osteoneogenesis, or new bone formation. Matrix or scaffold means the structural component or substrate intrinsically having a 3 dimensional form upon which the specific cellular events involved in bone formation will occur. The osteoconductive matrix allows for the ingrowth of host capillaries, perivascular tissue and osteoprogenitor cells. The osteoconductive matrix can also include an osteoinductive agent for providing osteogenic potential. An osteoinductive agent stimulates the host to build new bone.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "RankL inhibitor" refers to compounds or agents that inhibit the activity of RankL. RankL (Receptor Activator for Nuclear Factor κB Ligand), is important in bone metabolism by activating osteoclasts. RankL inhibitors include, but are not limited to, the human monoclonal antibody denosumab. One of skill in the art will appreciate that other RankL inhibitors are useful in the present invention.

III. Compounds

The compounds useful in the methods of the present invention include boldine and boldine derivatives. In some embodiments, the compounds of the present invention have Formula I:

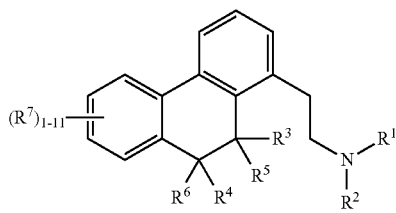

(I)

wherein each $R^1$, $R^2$, $R^4$, $R^5$, $R^6$, and $R^7$ is independently H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, —$OR^8$, —$C_{0-6}$ alkyl-$NR^8R^9$, —$SR^8$, —$C(O)R^8$, —$C_{0-6}$ alkyl-$C(O)OR^8$, —$C(O)NR^8R^9$, —$N(R^8)C(O)R^9$, —$N(R^8)C(O)OR^9$, —$N(R^8)C(O)NR^8R^9$, —$OP(O)(OR^8)_2$, —$S(O)_2OR^8$, —$S(O)_2NR^8R^9$, —CN, $C_{0-6}$ alkyl-cycloalkyl, heterocycloalkyl, $C_{0-6}$ alkyl-aryl or heteroaryl, wherein $R^2$ or $R^4$ combines with $R^3$ to form a bond. Alternatively, $R^4$ and $R^6$ combine to form =O. In addition, $R^8$ and $R^9$ are each independently H or $C_{1-6}$ alkyl. The compounds include the salts, hydrates, prodrugs and isomers thereof. Thereby promoting bone growth in the subject.

The compounds of Formula I are also represented by the following formula, describing in more detail the positions of the $R^7$ groups as $R^{7a}$, $R^{7b}$, $R^{7c}$ and $R^{7d}$:

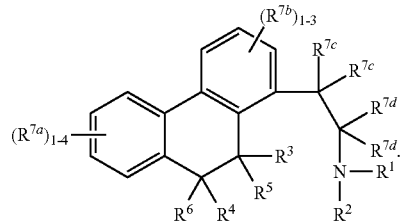

In some embodiments, each of $R^{7a}$, $R^{7b}$, $R^{7c}$ and $R^{7d}$ are independently selected from the group defined by $R^7$. In other embodiments, each of $R^{7a}$, $R^{7b}$, $R^{7c}$ and $R^{7d}$ are independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, —$OR^8$, —$C_{0-6}$ alkyl-$NR^8R^9$, —$SR^8$, —$C(O)R^8$, —$C_{0-6}$ alkyl-$C(O)OR^8$, —$C(O)NR^8R^9$, —$N(R^8)C(O)R^9$, —$N(R^8)C(O)OR^9$, —$N(R^8)C(O)NR^8R^9$, —$OP(O)(OR^8)_2$, —$S(O)_2OR^8$, —$S(O)_2NR^8R^9$, —CN, $C_{0-6}$ alkyl-cycloalkyl, heterocycloalkyl, $C_{0-6}$ alkyl-aryl and heteroaryl.

In some embodiments, $R^1$ and $R^2$ are each H, $C_{1-6}$ alkyl, $C_{1-6}$ haloalkyl, $C_{2-6}$ alkenyl, $C_{1-6}$ alkyl-cycloalkyl, or $C_{1-6}$ alkyl-aryl. Each $R^4$, $R^5$, $R^6$, $R^{7a}$, $R^{7b}$, $R^{7c}$ and $R^{7d}$ is independently H, halogen, $C_{1-6}$ alkoxy, or OH, wherein $R^2$ or $R^4$ combines with $R^3$ to form a bond. Alternatively, $R^4$ and $R^6$ combine to form =O.

In other embodiments, the present invention provides compounds of formula Ia:

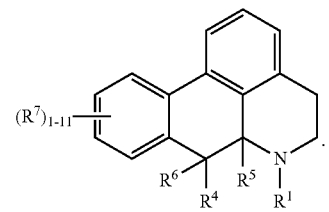

(Ia)

The compounds of Formula Ia are also represented by the following formula describing in more detail the positions of the $R^7$ groups as $R^{7a}$, $R^{7b}$, $R^{7c}$ and $R^{7d}$:

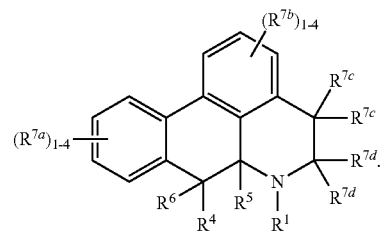

In some other embodiments, the compounds are of the formula:

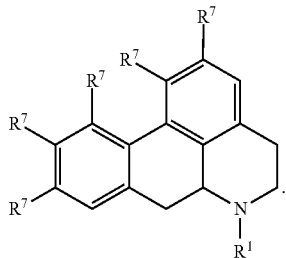

The compounds of the above formula are also represented by the following formula describing in more detail the positions of the $R^7$ groups as $R^{7a}$ and $R^{7b}$:

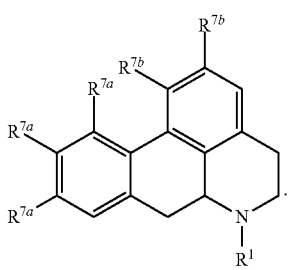

In still other embodiments, $R^1$ is $C_{1-6}$ alkyl; and each $R^{7a}$ and $R^{7b}$ is independently H, OMe, or OH. In yet other embodiments, the compounds are of the formula:

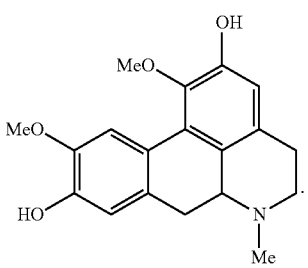

In still yet other embodiments, the compound is of the formula:

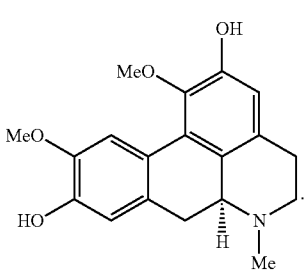

In some other embodiments, the compound is of formula Ib:

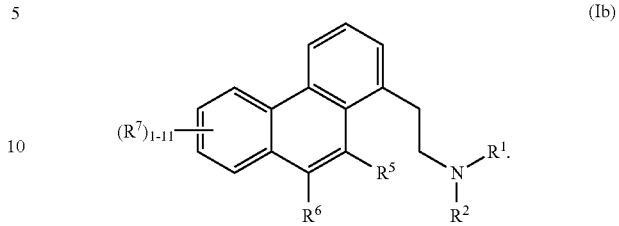

(Ib)

The compounds of Formula Ib are also represented by the following formula describing in more detail the positions of the $R^7$ groups as $R^{7a}$, $R^{7b}$, $R^{7c}$ and $R^{7d}$:

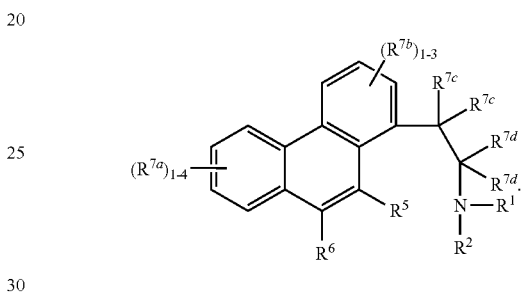

In still other embodiments, the compounds are of the formula:

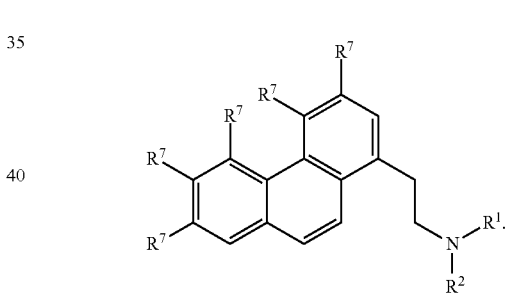

The compounds of Formula Ia are also represented by the following formula describing in more detail the positions of the $R^7$ groups as $R^{7a}$ and $R^{7b}$:

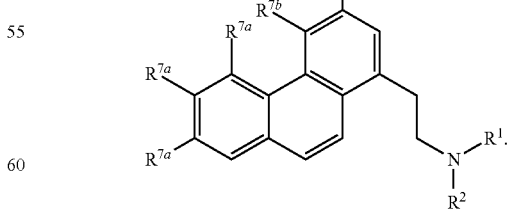

In yet other embodiments, $R^1$ and $R^2$ are each independently H or $C_{1-6}$ alkyl; and each $R^{7a}$ and $R^{7b}$ is independently H, OMe, or OH. In still yet other embodiments, the compound is:

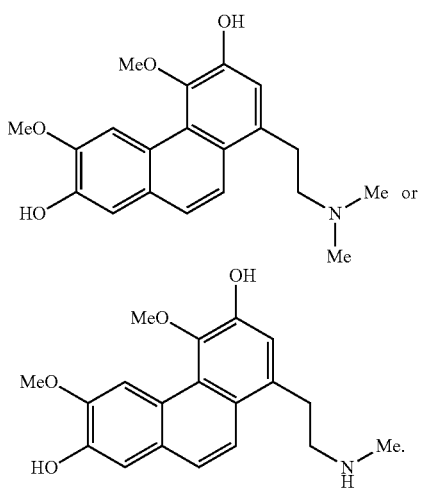

Compounds of Formula I useful in the methods of the present invention are described in the table below.

TABLE I

Compounds

| Compound | R¹ | R² | R³ | R⁴ | R⁵, R⁶, R⁷ᵃ, R⁷ᵇ, R⁷ᶜ & R⁷ᵈ* |
|---|---|---|---|---|---|
| 1 | Me | bond | H | | 1,10-OMe; 2,9-OH |
| 2 | Me | bond | H | | 1,9-OH; 2,10-OMe |
| 3 | Me | bond | H | | 1,10-OH; 2,9-OMe |
| 4 | Me | bond | H | | 1,11-OH; 2,10-OMe |
| 5 | Me | bond | H | | 1,10-OH; 2,11-OMe |
| 6 | Me | bond | H | | 1,2-OH; 9,10-OMe |
| 7 | Me | bond | H | | 1,9,10-OMe; 2-OH |
| 8 | Me | bond | H | | 1,2,10-OMe; 9-OH |
| 9 | Me | bond | H | | 1-OH; 2,9,10-OMe |
| 10 | Me | bond | H | | 1,2,10-OMe; 11-OH |
| 11 | Me | bond | H | | 1-OH; 2,10,11-OMe |
| 12 | Me | bond | H | | 1-OH; 2,11-OMe |
| 13 | Me | bond | H | | 1-OH; 2,10-OMe |
| 14 | Me | bond | H | | 1,2-OMe; 11-OH |
| 15 | Me | bond | H | | 1-OH; 2,10,11-OMe |
| 16 | Me | bond | H | | 1,2,9,10-OMe |
| 17 | Me | bond | H | | 1,2,10,11-OMe |
| 18 | Me | bond | H | | 1,2,3-OMe; 11-OH |
| 19 | Me | bond | H | | 1,2,9,10-OH |
| 20 | Me | bond | H | | 1-OH; 2,3,9,10-OMe |
| 21 | Me | bond | H | | 2-OMe; 10,11-OH |
| 22 | Me | bond | H | | 1-OMe; 2-OH |
| 23 | Me | bond | H | | 1,2,10-OMe |
| 24 | Me | bond | H | | 1-OH; 2-OMe |
| 25 | Me | bond | H | | 10-OMe; 11-OH |
| 26 | Me | bond | H | | 10-OH; 11-OMe |
| 27 | Me | bond | H | | 1,2-OH |
| 28 | Me | bond | H | | 1,2-OMe |
| 29 | Me | bond | H | | 2,10-OH |
| 30 | Me | bond | H | | 10,11-OH |
| 31 | Me | bond | H | | 1,2,3,9,10-OMe |
| 32 | Et | bond | H | | 1-OH; 2-OMe |
| 33 | n-Bu | bond | H | | 1,2,10-OMe; 9-OH |
| 34 | Me | bond | H | | 9,10-OH |

TABLE I-continued

Compounds

| Compound | R¹ | R² | R³ | R⁴ | R⁵, R⁶, R⁷ᵃ, R⁷ᵇ, R⁷ᶜ & R⁷ᵈ* |
|---|---|---|---|---|---|
| 35 | Me | bond | H | | 2-F; 10,11-OH |
| 36 | Et | bond | H | | 1,2-OMe |
| 37 | Me | bond | H | | 1,4-OH; 2,10,11-OMe |
| 38 | n-Pr | bond | H | | 2-OMe; 10,11-OH |
| 39 | Me | bond | H | | 1,2,9,10-OMe; 7-OH |
| 40 | Benzyl | bond | H | | 1-OH; 2-OMe |
| 41 | n-Pr | bond | H | | 1-OH; 2-OMe |
| 42 | n-Pr | bond | H | | 10-OMe; 11-OH |
| 43 | n-Pr | bond | H | | 10-OH; 11-OMe |
| 44 | Benzyl | bond | H | | 1,2-OMe |
| 45 | n-Pr | bond | H | | 1,2-OMe |
| 46 | Me | bond | H | | 10-Me; 11-OH |
| 47 | n-Pr | bond | H | | 10,11-OH |
| 48 | Me | bond | H | | 8-OH |
| 49 | 2-Cl—Et | bond | H | | 10,11-OH |
| 50 | 2-Propenyl | bond | H | | 1-OH; 2-OMe |
| 51 | H | bond | H | | 1-OH; 2,10-OMe |
| 52 | 2-Propenyl | bond | H | | 1,2-OMe |
| 53 | Me | bond | H | | 1,2,10-OMe; 7-oxo |
| 54 | 3-F—Pr | bond | H | | 10,11-OH |
| 55 | n-Pr | bond | H | | 1,2,11-OMe; 10-OH |
| 56 | H | bond | H | | 1-OH; 2,3,9,10-OMe |
| 57 | H | bond | H | | 1,3-OMe; 2-OH |
| 58 | 2-Propenyl | bond | H | | 10,11-OH |
| 59 | H | bond | H | | 1,2-OMe; 3-OH |
| 60 | H | bond | H | | 2,11-OH; 10-OMe |
| 61 | H | bond | H | | 1-OMe; 2-OH |
| 62 | H | bond | H | | 1-OH; 2-OMe |
| 63 | H | bond | H | | 1,2,3,9,10-OMe |
| 64 | H | bond | H | | 1,2-OMe |
| 65 | H | bond | H | | 1,4-OH; 2,9,10-OMe |
| 66 | —CH₂-cyclopropyl | bond | H | | 1-OH; 2-OMe |
| 67 | n-Pr | bond | H | | 11-OH |
| 68 | 2-Ph—Et | bond | H | | 10,11-OH |
| 69 | n-Pr | bond | H | | 2,10,11-OH |
| 70 | Me | bond | H | | 11-OH |
| 71 | n-Pr | bond | H | | 2-F; 10,11-OH |
| 72 | Me | bond | H | | 1,2,9,10-OMe; 3-CH₂OH |
| 73 | Benzyl | bond | H | | 1,2,11-OMe; 10-OH |
| 74 | i-Bu | bond | H | | 1,2,11-OMe; 10-OH |
| 75 | n-Bu | bond | H | | 1,2,11-OMe; 10-OH |
| 76 | 2-Cl—n-Bu | bond | H | | 10,11-OH |
| 77 | Me | Me | bond | | 1-OH; 2,9,10-OMe |
| 78 | Me | Me | bond | | 1-OH; 2,10,11-OMe |
| 79 | Me | Me | bond | | 1,2-OMe; 7-Me |
| 80 | Me | Me | bond | | 10,11-OH |
| 81 | Me | Et | bond | | 10,11-OH |

*R⁵, R⁶, R⁷ᵃ, R⁷ᵇ, R⁷ᶜ and R⁷ᵈ are each H unless noted otherwise.

The compounds of the present invention also include the salts, hydrates, solvates and prodrug forms. The compounds of the present invention also include the isomers and metabolites of those described in Formula I. For example, boldine can be the R-isomer or the S-isomer, or a mixture thereof.

The compounds of the present invention can be in the salt form. Salts include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases include alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine. In some embodiments, the present invention provides the hydrochloride salt. In other embodiments, the compound is boldine hydrochloride.

The compounds of the present invention can be made by a variety of methods known to one of skill in the art (see *Comprehensive Organic Transformations* Richard C. Larock, 1989). One of skill in the art will appreciate that other methods of making the compounds are useful in the present invention.

IV. Administration

In some embodiments, the present invention provides a pharmaceutical composition including a pharmaceutically acceptable excipient and a compound of Formula I. In other embodiments, the composition further comprises an osteoconductive matrix.

The compounds and compositions of the present invention can be administered locally or systemically.

A. Local Delivery

It also has been found that successful implantation of the compounds of the present invention for bone formation requires association of the compounds with a suitable carrier material capable of maintaining the compound at an in vivo site of application. The carrier can be biocompatible, a matrix, in vivo biodegradable and porous enough to allow cell infiltration.

The Sost or Wise antagonists are useful in clinical applications in conjunction with a suitable delivery or support system (matrix). As disclosed herein, the matrix can be combined with Sost or Wise antagonist to induce bone formation reliably and reproducibly in a mammalian body. The matrix preferably includes particles of porous materials. The pores are preferred to be of a dimension to permit progenitor cell migration into the matrix and subsequent differentiation and proliferation. The particle size can be within the range of 70 um-850 um, preferably 70 um-420 um, most preferably 150 um-420 um. It can be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation.

In some embodiments, the matrix can be an osteoconducive matrix. The osteoconducive matrix can include an osteoinductive agent and, optionally, a structural support. The osteoinductive agent can be any agent that promotes bone formation. In some embodiments, the osteoinductive agent can be bone allograft, bone autograft, demineralized bone or periodontal ligament cells. The osteoconductive matrix can also include a structural support such as a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic and polytetrafluoroethylene.

Other useful matrix materials include, for example, collagen; homopolymers or copolymers of glycolic acid, lactic acid, and butyric acid, including derivatives thereof; and ceramics, hydroxyapatite, tricalcium phosphate and other calcium phosphates, and calcium sulphates. Other matrices useful in the present invention include, but are not limited to, Kryptonite bone cement (Doctors Research Group, Oxford, Conn.) and Genex bone graft (Biocomposites, Wilmington, N.C.). Combinations of these matrix materials also can be useful.

When the SOST antagonist candidate is delivered in a carrier, the control solution is ideally the carrier absent the SOST antagonist candidate. Multiple doses of the SOST antagonist candidate can be applied to the test animal, preferably following a predetermined schedule of dosing. The dosing schedule can be over a period of days, more preferably over a period of weeks.

B. Systemic Delivery

In an exemplary embodiment, localized injection in situ of a SOST antagonist candidate, can be made into a test animal, with a control animal receiving an equal volume of control solution without the SOST antagonist candidate. Suitable dosage will depend on the nature of the particular SOST antagonist candidate being tested. By way of example, in dosing it should be noted that systemic injection, either intravenously, subcutaneously or intramuscularly, can also be used. Dosing performed by nebulized inhalation, eye drops, or oral ingestion should be at an amount sufficient to produce blood levels of the SOST antagonist candidate similar to those reached using systemic injection. The amount of SOST antagonist candidate that must be delivered by nebulized inhalation, eye drops, or oral ingestion to attain these levels is dependent upon the nature of the inhibitor used and can be determined by routine experimentation.

Individuals to be treated using methods of the present invention can be any mammal, for example local increase in bone can be used for fracture healing, fusion (arthrodesis), orthopedic reconstruction, and periodontal repair. Systemic increase in bone would be for treatment of low bone mass, i.e. osteoporosis. Such individuals include a dog, cat, horse, cow, or goat, particularly a commercially important animal or a domesticated animal, more particularly a human.

In therapeutic use SOST antagonists generally will be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the SOST antagonist.

A pharmaceutically acceptable carrier may include physiologically acceptable compounds that act, for example, to stabilize the SOST antagonist or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SOST antagonist and on its particular physio-chemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The methods of the present invention include application of SOST antagonists in cocktails including other medicaments, for example, antibiotics, fungicides, and anti-inflammatory agents. Alternatively, the methods may comprise sequential dosing of an afflicted individual with a SOST antagonist and one or more additional medicaments to optimize a treatment regime. In such optimized regimes, the medicaments, including the granulation inhibitor can be applied in any sequence and in any combination.

The SOST, Wise, or LRP antagonists of the present invention may also be included in slow release formulations for prolonged treatment following a single dose. In one embodiment, the formulation is prepared in the form of microspheres. The microspheres can be prepared as a homogenous matrix of a SOST antagonist with a biodegradable controlled release material, with optional additional medicaments as the treatment requires. The microspheres are preferably prepared in sizes suitable for infiltration and/or injection, and injected systemically, or directly at the site of treatment.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The amount of SOST, Wise, or LRP antagonists administered to an individual will depend, in part, on the disease and/or extent of injury. Methods for determining an effective amount of an agent to administer for a diagnostic or a therapeutic procedure are well known in the art and include phase I, phase II and phase III clinical trials, or the Pilot and Pivotal trials (FDA device approval pathway). Generally, an agent antagonist is administered in a dose of about 0.01 to 200 mg/kg body weight when administered systemically, and at a concentration of approximately 0.1-100 µM when administered directly to a wound site. The total amount of SOST antagonist can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular SOST antagonist required to provide an effective amount to a region or regions of injury depends on many factors including the age and general health of the subject as well as the route of administration, the number of treatments to be administered, and the nature of the SOST antagonist. In view of these factors, the skilled artisan would adjust the particular dose so as to obtain an effective amount for efficaciously promoting bone formation for therapeutic purposes.

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra).

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

V. Orthopedic and Periodontal Devices

In some embodiments, the present invention provides an orthopedic or periodontal medical device formed from a structural support, wherein an implantable portion of the structural support is adapted to be permanently implanted within a subject, wherein the implantable portion is attached to a bone, the structural support bearing at least a partial external coating including a compound of the present invention.

Other aspects of the present invention are directed towards medical implants. Such medical devices and implants include, for example, the osteogenic devices and methods of using the same for repairing endochondral bone and osteochondral defects taught in US patent application publication No. 20060177475 to David Rueger et al., published Aug. 10, 2006, as well as in issued U.S. Pat. Nos. 6,190,880, 5,344,654, 5,324,819, 5,468,845, 6,949,251, 6,426,332 and 5,656,593, and U.S. Publication Nos. 2002/0169122, 2002/0187104, 2006/0252724 and 2007/0172479, the subject matter of which is hereby incorporated by reference.

These medical devices generally provide a structural support having an implantable portion preferentially adapted to mechanically engage bone and/or cartilage as taught, for instance, in U.S. Publication No. 2006/0178752 to Joseph Vaccarino III, et al., published Aug. 10, 2006, the subject matter of which is hereby incorporated by reference. These bone implants desirably comprise an active agent on at least a portion thereof. As shown by U.S. Publication No. 2006/0188542 to John Dennis Bobyn, et al., published Aug. 24, 2006, the subject matter of which is hereby incorporated by reference, the active agent is preferably formulated to be locally deliverable to bone proximate the implant in sustained-release or in at least a two-phased release scheme. In the latter, a first phase rapidly releases a first quantity of the active agent, and the second and subsequent phases gradually release a second quantity of the active agent, whereby bone formation stimulated by the active agent is modulated.

Medical devices such as bone implants feature implantable portions bearing Sost antagonists foster quicker and more complete bone formation in situ. The implantable portion of the medical device can be desirable at least partially or totally covered or impregnated with a Sost antagonist. In some embodiments, the external coating completely coats the implantable portion of the structural support.

In some other embodiments, the implantable portion of the structural support comprises an osteoconductive matrix. The matrix material can be conducive to bone growth. This can be desirable for materials such as teeth and artificial bone graft sections, and the like. Alternatively, when the implantable sections are load bearing and formed, e.g., of stainless steel, these implantable sections can be desirable when formed with a Sost antagonist coating. In that event, it is desirable to also provide a separate matrix material conducive to forming new bone growth.

Suitable matrixes include those comprising composite biomaterials having a sponge-like structure such as those containing, e.g., phosphophoryn and/or collagen as taught in Takashi Saito's U.S. Publication No. 2006/0188544, published Aug. 24, 2006, the subject matter of which is hereby incorporated by reference. Such coatings include, for example, the single and multilayer coatings taught in U.S. Publication No. 2006/0204542 to Zongtao Zhang et al, published Sep. 14, 2006, as well as those in U.S. Pat. Nos. 6,949,251, 5,298,852, 5,939,039, and 7,189,263 and can be made by conventional methods including the methods taught therein, the subject matter of which is hereby incorporated by reference.

The matrix can be part of the device of the present invention. In other embodiments, the osteoconductive matrix includes an osteoinductive agent such as bone allograft, bone autograft, demineralized bone or periodontal ligament cells. In some other embodiments, the osteoconductive matrix includes a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic and polytetrafluoroethylene. One of skill in the art will appreciate that other osteoconductive matrices and osteoinductive agents are useful in the present invention.

VI. Assay for Identification of Compounds for Treating Bone Loss

Compounds useful in the methods of the present invention can be identified via a variety of methods known to one of skill in the art. Several exemplary methods for identifying such antagonists are described herein, including cell-based and in vitro techniques (Journal of Bone and Mineral Research 2006, 21(11), 1738-1749). A general method of identifying SOST antagonists involves evaluating the effects of antagonist candidates on bone formation under controlled conditions. Preferably bone formation is determined using micro-CT techniques on live animals. Preferred animals include rodents, more preferred are primates. Femur, tibia and vertebrae bones are particularly useful subjects for such study.

Briefly, the test animal is treated with a predetermined dose of a SOST antagonist candidate. A control animal is treated with a control solution, preferably a non-irritating buffer solution or other carrier.

Once the dosing schedule has been completed, both test and control animals are examined to determine the quantity of bone formation present. This can be accomplished by any suitable method, but is preferably performed on live animals to analyze the bone mineral content. Methods for micro-CT examination of bones in animals are well known in the art. A SOST antagonist candidate suitable for use as a SOST antagonist is identified by noting significant bone formation in the test animal when compared to the control animal. Bone formation in the test bone(s) of the test animal can be 0.5%, 1, 5, 10, 20, 30, 40, 50, 60, 70, 80, 90, 100, 200, 300, 400, 500, 600, 700, 800, 900 or 1000% more bone formation than is present in the same bones of the control animal. More preferably, bone formation can be 20%, most preferably 30% or 40%. Where necessary, levels of bone formation can be calculated by determining the volume of bone formation present in each animal. Calculations can be performed by constructing a 3-dimensional image of the bone formation and calculating the volume from the image with the aid of e.g., histomorphometry.

An example of the molecular modeling system described generally above consists of the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

SOST antagonists may also be identified using a process known as computer, or molecular modeling, which allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

VII. Method of Promoting Bone Growth

In some embodiments, the present invention provides a method of promoting bone growth in a subject in need thereof, by administering to the subject a therapeutically effective amount of a compound of the present invention.

Bone growth can be measured in a variety of ways known to one of skill in the art. Methods of measuring bone growth include, but are not limited to, Uct (micro CT), Dual X-ray absorption (Bone density), ultrasound, QCT, SPA, DPA, DXR, SEXA, QUS, X-ray, using the human eye during surgically manipulation, Alizarin red S, serum osteocalcin, serum alkaline phosphatase, Serum bone Gla-protein (BGP), bone mineral content, serum calcium, serum phosphorus, tantalum markers, and serum IGF-1.

Many indicators of bone growth can be used to measure bone growth, including bone density. In some embodiments, bone growth can be demonstrated by an increase of 0.1% in bone density. In other embodiments, bone growth can be demonstrated by an increase of 0.2, 0.3, 0.4, 0.5, 0.6, 0.7, 0.8, 0.9, 1.0, 5, 10, 20, 30, 40, 50, 60, 70, 80, 90, 100, 200, 300, 400, 500, 600, 700, 800, 900 or 1000% or greater, in bone density.

One of skill in the are appreciates that bone growth be local, systemic or both.

A. Local Bone Growth

In some embodiments, the present invention provides a method of promoting bone growth at a site of injury or localized condition. A subject in need of local bone growth can suffer from a variety of ailments and disease states. In other embodiments, the injury can be a fracture or weakened bone. In some other embodiments, the subject can be in need of a spinal fusion, arthrodesis or an orthopedic or periodontal synthetic bone graft or implant.

The local bone growth of the present invention can be achieved in a variety of methods. In some embodiments, the method further comprises administering to the subject an osteoconductive matrix, as described above. The matrix can be part of the device of the present invention, as described above. In other embodiments, the osteoconductive matrix includes an osteoinductive agent such as bone allograft, bone autograft, demineralized bone or periodontal ligament cells. In some other embodiments, the osteoconductive matrix includes a calcium salt, calcium sulfate, calcium phosphate, a calcium phosphate cement, hydroxyapatite, coralline based hydroxyapatite (HA), dicalcium phosphate, tricalcium phosphate (TCP), calcium carbonate, collagen, plaster of Paris, phosphophoryn, a borosilicate, a biocompatible ceramic, a calcium phosphate ceramic and polytetrafluoroethylene.

B. Systemic Bone Growth

In other embodiments, the present invention provides a method of promoting systemic bone growth. Systemic bone growth refers to the growth of bone throughout the subject, and can effect all the bones in the subject's body. A subject in need of systemic bone growth can suffer from a variety of ailments and disease states. In some embodiments, the subject suffers from a low bone mass phenotype disease. Low bone mass can be determined by a variety of methods known to one of skill in the art. For example, low bone mass can be characterized by a T-score less than about −1. Low bone mass phenotype diseases can include osteoporosis, osteopenia, and osteoporosis-pseudoglioma syndrome (OPPG). In some other embodiments, the low bone mass phenotype disease can be osteopenia or osteoporosis-pseudoglioma syndrome (OPPG).

The methods of the present invention can also be used to treat diseases characterized by secondary induced osteoporosis (low bone mass) including, but not limited to, osteomalacia, Polyostotic fibrous dysplasia, Paget's disease, rheumatoid arthritis, zero gravity, osteoarthritis, Prolonged inactivity or immobility, osteomyelitis, Celiac disease, Crohn's Disease, Ulcerative Colitis, inflammatory bowel disease, gastrectomy, secondary induced osteoporosis, Amennorhea, Cushing's Disease, Cushing's syndrome, Diabetes Mellitus, Diabetes, Eating Disorders, Hyperparathyroidism, Hyperthyroidism, Hyperprolactinemia, Kleinefelter Syndrome, Thyroid Disease, Turner Syndrome, steroid induced osteoporosis, seizure or depression induced osteoporosis, immobility, arthritis, cancer induced secondary osteoporosis, Gonadotropin-releasing hormone agonists induced low bone mass, Thyroid medication induced low bone mass, Dilantin (phenyloin), depakote induced low bone mass, chemotherapy induced low bone mass, Immunosuppressant induced low bone mass, Blood thinning agents induced low bone mass, Grave's disease, Juvenile rheumatoid arthritis, Malabsorption syndromes, Anorexia nervosa, Kidney disease, Anticonvulsant treatment (e.g., for epilepsy), Corticosteroid treatment (e.g., for rheumatoid arthritis, asthma), Immunosuppressive treatment (e.g., for cancer), Inadequate nutrition (especially calcium, vitamin D), Excessive exercise leading to amenorrhea (absence of periods), Smoking, and Alcohol abuse, pregnancy-associated osteoporosis, copper deficiency, Dibasic aminoaciduria type 2, Werner's syndrome, Hajdu-Cheney syndrome, Hyperostosis corticalis deformans juvenilis, Methylmalonic aciduria type 2, Cystathionine beta-synthase deficiency, Exemestane, Hyperimmunoglobulin E (IgE) syndrome, Haemochromatosis, Singleton-Merten syndrome, Beta thalassaemia (homozygous), Reflex sympathetic osteodystrophy, Sarcoidosis, Winchester syndrome, Hallermann-Streiff syndrome (HSS), Cyproterone, Glycerol kinase deficiency, Bonnet-Dechaume-Blanc syndrome, Prednisolone, Heparin, Geroderma osteodysplastica, Torg osteolysis syndrome, Orchidectomy, Fabry's disease, Pseudoprogeria syndrome, Wolcott-Rallison syndrome, Ankylosing spondylitis, Myeloma, Systemic infantile hyalinosis, Albright's hereditary osteodystrophy, Anorexia Nervosa, Autoimmune Lymphoproliferative Syndrome, Brown-Sequard Syndrome, Diamond-Blackfan anemia, Eating disorders, Galactorrhoea-Hyperprolactinaemia, Gonadal dysgenesis, Kidney conditions, Menkes Disease, Menopause, Neuritis, Ovarian insufficiency due to FSH resistance, Familial Ovarian insufficiency, Premature aging, Primary biliary cirrhosis, Prolactinoma, Familial Prolactinoma, Renal osteodystrophy, Ulcerative colitis, Underweight, Werner syndrome, Bone tumor, Bone cancer, Brittle bone disease, Osteogenesis imperfecta congenita, and Osteogenesis imperfecta tarda. One of skill in the art will appreciate that other types of conditions, diseases and treatments lead to osteoporosis.

Following administration of the compounds of the present invention, systemic bone growth can be determined by a variety of methods, such as improvements in bone density. Bone density can be measured by a variety of different methods, including the T-score and Z-score. The Z-score is the number of standard deviations above or below the mean for the patient's age and sex. The T-score is the number of standard deviations above or below the mean for a healthy 30 year old adult of the same sex as the patient. Low bone mass is characterized by a T-score of −1 to −2.15. Osteoporosis is characterized by a T-score less than −2.15. Improvement in the T-score or Z-score indicate bone growth. Bone density can be measured in a variety of places of the skeleton, such the spine or the hip. One of skill in the art will appreciate that other methods of determining bone density are useful in the present invention.

C. Promoting Bone Growth with a Compound of the Present Invention and an Antiresorptive Drug In some other embodiments, the method of the present invention promotes bone growth by administering the compound of Formula I with an antiresorptive drug. Antiresorptive drugs include those that slow or block the resorption of bone. Administration of a compound of Formula I and an antiresorptive drug can promote local bone growth and/or systemic bone growth. In some embodiments, the administration of a compound of Formula I and an antiresorptive drug promotes systemic bone growth. Bone growth can be achieved by increasing bone mineral content, increasing bone density and/or growth of new bone. In other embodiments, local application of the compound of Formula I and an antiresorptive drug achieves systemic bone growth.

Antiresorptive drugs useful in the methods of the present invention include, but are not limited to, denosumab, a RankL inhibitor, a bisphosphonate, a selective estrogen receptor modulator (SERM), calcitonin, a calcitonin analog, Vitamin D and a Vitamin D analog.

In other embodiments, the antiresorptive drug can be a bisphosphonate (i.e. fosamax, actonel, reclast), a parathyroid hormone (PTH) or analog (i.e. teriparatide (Forteo)), calcitonin or analog (i.e. Miacalcic), Vitamin D or analog, SERM or analog (i.e. Evista).

Bisphosphonates useful in the methods of the present invention can be any suitable bisphosphonate. In some embodiments, the bisphosphonates are nitrogenous, such as Pamidronate (APD, Aredia), Neridronate, Olpadronate, Alendronate (Fosamax), Ibandronate (Boniva), Risedronate (Actonel) and Zoledronate (Zometa). In other embodiments, the bisphosphonates are non-nitrogenous, such as Etidronate (Didronel), Clodronate (Bonefos, Loron) and Tiludronate (Skelid). One of skill in the art will appreciate that other bisphosphonates are useful in the present invention.

SERMs useful in the methods of the present invention can be any suitable SERM. In some embodiments, the SERM can be clomifene, raloxifene, tamoxifen, toremifene, bazedoxifene, lasofoxifene or ormeloxifene. One of skill in the art will appreciate that other SERMs are useful in the present invention.

The antiresorptive drug can also be any suitable calcitonin analog. In some embodiments, calcitonin analogs useful in the methods of the present invention include, but are not limited to, miacalcic. One of skill in the art will appreciate that other calcitonin analogs are useful in the present invention.

Vitamin D analogs useful in the methods of the present invention can be any suitable Vitamin D analog. In some embodiments, Vitamin D analogs useful in the methods of the present invention include, but are not limited to, Vitamin D1 (molecular compound of ergocalciferol with lumisterol, 1:1), Vitamin D2 (ergocalciferol or calciferol), Vitamin D3 (cholecalciferol), Vitamin D4 (22-dihydroergocalciferol) and Vitamin D5 (sitocalciferol). One of skill in the art will appreciate that other Vitamin D analogs are useful in the present invention.

RankL inhibitors useful in the present invention include any compounds that inhibit the activity of RankL. For example, RankL inhibitors include, but are not limited to, the human monoclonal antibody denosumab. One of skill in the art will appreciate that other RankL inhibitors are useful in the present invention.

VIII. Treating Renal Damage

In some embodiments, the present invention provides a method of treating renal damage by administering to a subject suffering from renal damage, a therapeutically effective amount of a compound of Formula I.

Renal damage can be caused by a variety of ailments known to one of skill in the art. In some embodiments, renal damage is caused by infection, radiation, toxin, dehydration or trauma. Toxins causing renal damage include, but are not limited to, chemicals, poisons, and chemotherapeutic agents. One of skill in the art will appreciate that other causes of renal damage can be treated by the methods of the present invention.

Renal damage treatable by the compounds of the present invention includes acute renal failure. Acute renal failure is also known as acute kidney failure or acute kidney injury. Acute renal failure results in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, and effects on other organ systems. Acute renal failure can be characterized by oliguria or anuria (decrease or cessation of urine production), although nonliguric acute renal failure can also occur.

A subject can be characterized as being at (1) a risk for acute damage; (2) kidney damage resulting in injury; (3) acute renal failure; and (4) loss of kidney function. Risk for acute kidney damage is characterized by serum creatinine increased 1.5 times or urine production of <0.5 ml/kg body weight over 6 hours. Injury is reached when serum creatinine increased 2.0 times or urine production<0.5 ml/kg over 12 hours. Failure is reached when serum creatinine increased 3.0 times or creatinine>355 µM (with a rise of >44) or urine output below 0.3 ml/kg over 24 hours. Loss of kidney function is reached when a subject suffers from persistent acute renal failure or more than four weeks of complete loss of kidney function.

Kidney biopsy can be performed in the setting of acute renal failure, to provide a definitive diagnosis and sometimes an idea of the prognosis, unless the cause is clear and appropriate screening investigations are reassuringly negative.

Renal therapeutic agents of the invention can be used in subjects that have received renal injury, or those at risk of chronic renal failure. As used herein, a subject is said to be in, or at risk for, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which can be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

IX. Treating Cancer

The compounds and compositions of the present invention are also useful in the treatment of cancer. The compounds of formula I can possess anti-proliferative activity and are therefore useful in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. Using such cell line and enzymes assays it may be determined whether a compound is anti-proliferative in the context of the present invention.

As used herein, the term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. One of skill in the art will appreciate that other cancers and proliferative disorders can be treated by the compounds and compositions of the present invention.

In some embodiments, the cancer is bone cancer, colon cancer, multiple myeloma, gastric cancer, colorectal cancer, prostate cancer, cervical cancer, lung cancer, pancreatic cancer, medulloblastoma, liver cancer, parathyroid cancer, endometrial cancer, or breast cancer. In other embodiments, the cancer is bone cancer.

X. Examples

Example 1

Promotion of Bone Growth

Using the assay described above and in Journal of Bone and Mineral Research 2006, 21(11), 1738-1749 (incorporated herein in its entirety), compounds of the present invention can be identified as promoting bone growth. For example, the mouse test animal is treated with a predetermined dose of a SOST antagonist candidate for a complete dosing schedule. A control mouse is treated with a control solution, preferably a non-irritating buffer solution or other carrier. Once the dosing schedule has been completed, both test and control animals are examined with sacrifice using micro-CT to determine the quantity of bone formation present. Using this method, (S)-boldine was identified as promoting bone growth:

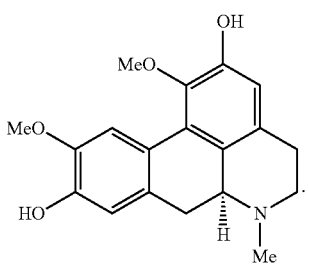

FIG. 1 shows (S)-boldine modulating the Wnt pathway to promote bone growth at doses of 2.5 ng ("low"), 60 ng ("medium"), and 125 ng ("high").

Example 2

Bone Growth with (S)-Boldine

Figure 2:
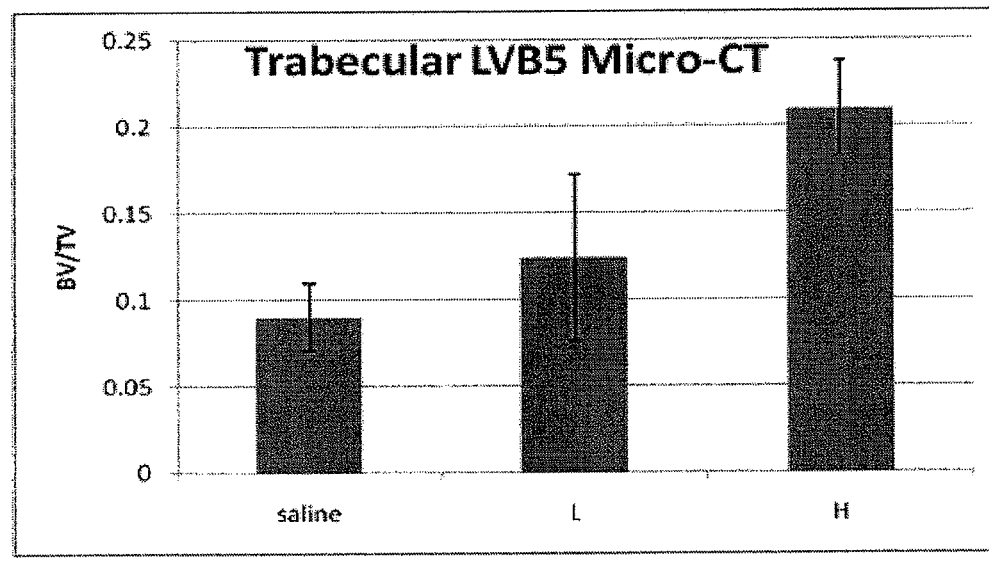
FIG. 2 shows bone density analysis measured by u-CT for the lumbar vertebrae 5 (LVBS) of mice treated with 0.75 ("L") or 75 ("H") mg/kg (via i.p) for 30 days, with a 65% increase over baseline at 75 mg/kg.

Four month old male C57BL/6 mice were treated daily with saline vehicle or the sclerostin inhibitor of (S)-boldine at 0.75 ("L") or 75 ("H") mg/kg (via i.p) for 30 days. Study endpoints included measurement of trabecular lumbar vertebrae 5 (LVB5) by uCT, showing 65% increase in bone volume over baseline at 75 mg/kg (FIG. 2). Histomorphometry of all animals in both the L and H groups demonstrated an increase in BV/TV of 78% in trabecular long bone over saline controls (p=0.05). pQCT measurements of femur resulted in an increase in BV/TV of 8% over baseline controls at 60 mg/kg of (S)-boldine.

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method of promoting bone growth in a subject in need thereof, comprising administering to the subject a therapeutically effective amount of a compound of the formula:

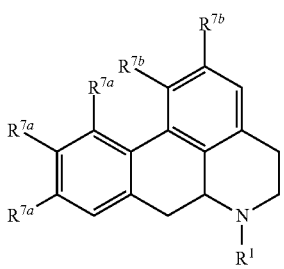

wherein
R$^1$ is selected from the group consisting of H and C$_{1-6}$ alkyl; and
each R$^{7a}$; and R$^{7b}$ is independently selected from the group consisting of H, C$_{1-6}$ alkyl, and —OR$^8$, wherein each R$^8$ is independently selected from the group consisting of H and C$_{1-6}$ alkyl;
or a salt, hydrate, prodrug, or isomer thereof, thereby promoting bone growth in the subject.

2. The method of claim 1, wherein
R$^1$ is C$_{1-6}$ alkyl; and
each R$^{7a}$ and R$^{7b}$ is independently selected from the group consisting of H and —OR$^8$.

3. The method of claim 1, wherein
R$^1$ is methyl; and
each R$^{7a}$; and R$^{7b}$ is independently selected from the group consisting of H, OH, and OMe.

4. The method of claim 1, wherein the compound is

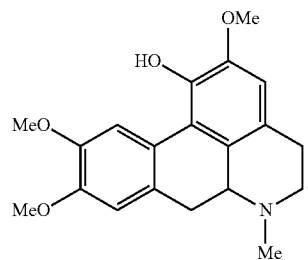

5. The method of claim 1, wherein the compound is

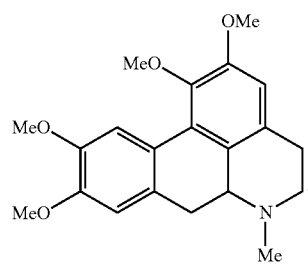

6. The method of claim 1, wherein the bone growth is promoted at a site of injury or localized condition.

7. The method of claim 6, further comprising the step of administering to the subject an osteoconductive matrix.

8. The method of claim 1, wherein the bone growth is systemic.

9. The method of claim 1, wherein the compound is administered in combination with an antiresorptive drug.

10. A method of treating renal damage, comprising administering to a subject in need thereof a therapeutically effective amount of a compound of the formula:

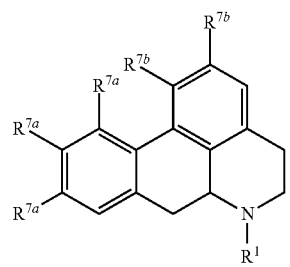

wherein
R$^1$ is selected from the group consisting of H and C$_{1-6}$ alkyl; and
each R$^{7a}$ and R$^{7b}$ is independently selected from the group consisting of H, C$_{1-6}$ alkyl, and —OR$^8$, wherein each R$^8$ is independently selected from the group consisting of H and C$_{1-6}$ alkyl;

or a salt, hydrate, prodrug, or isomer thereof, thereby treating renal damage in the subject.

11. An orthopedic or periodontal medical device comprising a structural support, wherein an implantable portion of the structural support is adapted to be permanently implanted within a subject, wherein the implantable portion is attached to a bone, the structural support bearing at least a partial external coating comprising a compound of the formula:

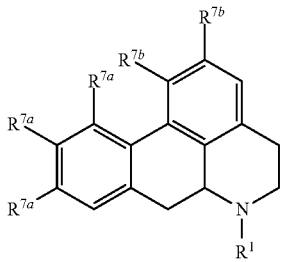

wherein
$R^1$ is selected from the group consisting of H and $C_{1-6}$ alkyl; and
each $R^{7a}$; and $R^{7b}$ is independently selected from the group consisting of H, $C_{1-6}$ alkyl, and —$OR^8$, wherein each $R^8$ is independently selected from the group consisting of H and $C_{1-6}$ alkyl;
or a salt, hydrate, prodrug, or isomer thereof.

12. A method of treating cancer, comprising administering to a subject in need thereof a therapeutically effective amount of a compound of the formula:

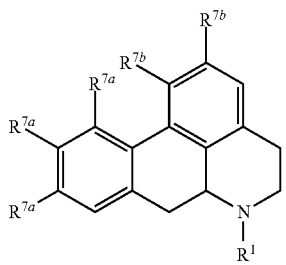

wherein
$R^1$ is selected from the group consisting of H and $C_{1-6}$ alkyl; and
each $R^{7a}$ and $R^{7b}$ is independently selected from the group consisting of H, $C_{1-6}$ alkyl, and —$OR^8$, wherein each $R^8$ is independently selected from the group consisting of H and $C_{1-6}$ alkyl;
or a salt, hydrate, prodrug, or isomer thereof,
wherein the cancer is selected from the group consisting of bone cancer, colon cancer, multiple myeloma, gastric cancer, colorectal cancer, prostate cancer, cervical cancer, lung cancer, pancreatic cancer, medulloblastoma, liver cancer, parathyroid cancer, endometrial cancer and breast cancer;
thereby treating cancer in the subject.

13. The method of claim 12, wherein the cancer is bone cancer.

* * * * *